US005210301A

United States Patent [19]

Saeki et al.

[11] Patent Number: 5,210,301

[45] Date of Patent: * May 11, 1993

[54] SQUARIUM COMPOUNDS, PROCESS FOR PREPARING THE SAME AND ELECTROPHOTOGRAPHIC PHOTORECEPTORS CONTAINING THE SAME

[75] Inventors: Satoshi Saeki; Seki Kin; Kaoru Torikoshi; Hiroyuki Tanaka; Lyong S. Pu, all of Kanagawa, Japan

[73] Assignee: Fuji Xerox Co., Ltd., Tokyo, Japan

[ * ] Notice: The portion of the term of this patent subsequent to Oct. 8, 2008 has been disclaimed.

[21] Appl. No.: 232,990

[22] Filed: Aug. 17, 1988

Related U.S. Application Data

[60] Division of Ser. No. 32,922, Mar. 20, 1987, abandoned, which is a continuation of Ser. No. 733,438, May 13, 1985, abandoned.

[30] Foreign Application Priority Data

May 11, 1984 [JP] Japan .................................. 59-92769
May 11, 1984 [JP] Japan .................................. 59-92771

[51] Int. Cl.$^5$ ........................................ C07C 211/43
[52] U.S. Cl. ........................................ 564/305; 430/73
[58] Field of Search ........................... 564/307; 430/73

[56] References Cited

U.S. PATENT DOCUMENTS

| | | | |
|---|---|---|---|
| 4,521,621 | 6/1985 | Yanus et al. | 564/307 |
| 4,523,035 | 6/1985 | Yanus et al. | 564/307 |
| 4,524,220 | 6/1985 | Law | 564/307 |
| 4,525,592 | 6/1985 | Law et al. | 564/307 |
| 4,552,822 | 11/1985 | Kazmaier et al. | 564/307 |
| 4,621,038 | 11/1986 | Kazmaier et al. | 564/307 |
| 4,624,904 | 11/1986 | Kazmaier et al. | 564/307 |
| 4,644,082 | 2/1987 | Law et al. | 564/307 |
| 4,746,756 | 5/1988 | Kazmaier | 564/307 |

OTHER PUBLICATIONS

Kin et al. Chemical Abstracts vol. 105 No. 8 entry #70134g (1986).
Takegawa et al. Chem. Abs. vol. 105 No. 16 entry #143544c (1986).
Law et al. Chem. Abs. vol. 108 No. 18 entry #152134h (1984).
Akasaki et al. Chem. Abs. vol. 108 No. 22 entry #195928n (1988).
Akasaki et al. Chem. Abs. vol. 108 No. 22 entry #195929p (1988).
Akasaki et al. Chem. Abs. vol. 108 No. 22 entry #195930g (1988).
Akasaki et al. Chem. Abs. vol. 108 No. 22 entry #195932 (1988).
Akasaki et al. Chem. Abs. vol. 109 No. 20 entry #180416r (1988).

*Primary Examiner*—Mukund J. Shah
*Assistant Examiner*—E. C. Ward
*Attorney, Agent, or Firm*—Sughrue, Mion, Zinn, Macpeak & Seas

[57] ABSTRACT

Novel squarium compounds which have a flat photosensitivity in the wide range from visible ray region to the near infrared ray region as a charge generator and which can be prepared by reacting squaric acid and an aniline derivative, and electrophotographic photoreceptors containing the squarium compounds are disclosed.

1 Claim, 1 Drawing Sheet

SQUARIUM COMPOUNDS, PROCESS FOR PREPARING THE SAME AND ELECTROPHOTOGRAPHIC PHOTORECEPTORS CONTAINING THE SAME

This is a division application Ser. No. 07/032,922 filed Mar. 20, 1987, which is a continuation of application Ser. No. 06/733,438 filed May 13, 1985 both now abandoned.

FIELD OF THE INVENTION

This invention relates to novel squarium compounds having a flat photosensitivity in the wide range from the visible ray region to the near infrared ray region as a charge generator, a process for preparing them and electrophotographic photoreceptors containing the squarium compounds.

BACKGROUND OF THE INVENTION

Hitherto, inorganic photographic materials such as amorphous selenium, selenium alloys, cadmium sulfide and zinc oxide and organic photographic materials represented by polyvinylcarbazole and polyvinylcarbazole derivatives are widely known as electrophotographic photoreceptors.

It is well known that amorphous selenium or selenium alloys have superior properties as electrophotographic photoreceptors and have been put into practical use. However, in producing these materials, a complicated vacuum deposition process is necessary, and further the vacuum-deposited film obtained has a disadvantage in that the film lacks flexibility. Zinc oxide is used as a dispersed photographic material in which zinc oxide is dispersed in a resin, but such material has problems such as a low mechanical strength and cannot be used repeatedly as is.

Polyvinylcarbazoles known as organic photoconductive materials have advantages such as transparency, good film-forming property and flexibility, but polyvinylcarbazoles per se have no photosensitivity in the visible ray region, and cannot be used practically alone. Accordingly, various sensitization methods have been proposed therefor. Although spectral sensitization of polyvinylcarbazole using a sensitizing dye has resulted in expanded spectral sensitivities extending to the visible ray region, a sufficient photographic sensitivity as electrophotographic photoreceptors cannot be obtained, and it still has a drawback in that photo-fatigue is remarkable.

On the other hand, spectral sensitization with an electron acceptor gives rise to electrophotographic photoreceptors having a sufficient photosensitivity, and some of them have been practically used. However, there are still more problems with mechanical strength and durability.

Various extensive studies have been made on photosensitive materials and there are many reports. However, electrophotographic photoreceptors having a superior electric characteristic and a sufficient photosensitivity have not yet been obtained. At present, there are reports about phthalocyanines which show superior electrophotographic characteristics as dispersed photosensitive materials. However, their spectral sensitivity is partial to the long wavelength region, and they have a drawback in that reproduction of red color is inferior.

SUMMARY OF THE INVENTION

An object of this invention is to provide novel squarium compounds having a flat photosensitivity in the wide range from the visible ray region to the near infrared ray region, a process for preparing squarium compounds and electrophotographic photoreceptors containing such squarium compounds.

Another object of this invention is to provide photoconductive materials having an extremely high photosensitivity, which are possible to use in every electrophotographic process and have a spectral sensitivity in the range from the visible ray region to the near infrared ray region.

A further object of this invention is to provide extremely superior electrophotographic photoreceptors having a flexibility that inorganic photographic materials fail to have, which are free from drawbacks of organic photographic materials such as polyvinylcarbazole-trinitrofluorenones, that is a low abrasion resistance and lack of mechanical strength, and which are superior in mechanical strength such as abrasion resistance and have a flat spectral sensitivity in the wide range from the visible ray region to the near infrared ray region.

As a result of extensive studies to obtain photoconductive materials having improved properties over conventional inorganic photographic materials, organic photographic materials or organic dispersed photographic materials, having superior electrophotographic properties and flexibility, and further having high photographic sensitivity in the wide range from the visible ray region to the near infrared ray region, the present inventors found that the squarium compounds represented by the following general formula (I) possess extremely superior characteristics:

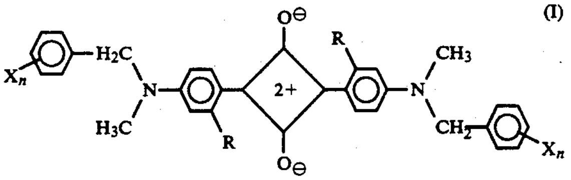

(I)

wherein X represents an electron attractive group, n represents 0 or an integer of from 1 to 3, and R represents a hydrogen atom or a methyl group.

In the FIGS. "1" represents an electroconductive support, "2" represents a charge generation layer, "3" represents a charge transport layer and "4" represents a photosensitive layer.

DETAILED DESCRIPTION OF THE INVENTION

The squarium compounds of this invention represented by formula (I) above can be prepared by reacting 3,4-di-hydroxy-3-cyclobutene-1,2-dione (hereinafter referred to as squaric acid) represented by formula (II):

(II)

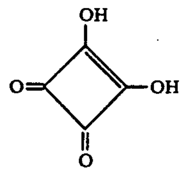

with an aniline derivative of formula (III):

(III)

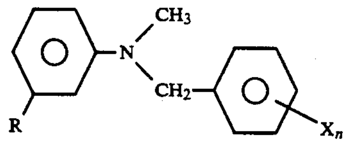

wherein X, R and n have the same meanings as above.

In formulae (I), (II) and (III), the electron attractive group represented by X includes, for example, a halogen atom, a nitro group, a cyano group, a formyl group, an acyl group, a carboxyl group and an alkoxycarbonyl group.

The reaction of squaric acid of formula (II) with an aniline derivative of formula (III) can be carried out by heating squaric acid and the aniline derivative in an inert organic solvent such as n-butyl alcohol or amyl alcohol at about 100° C. to about 140° C. for about 3 hours to about 5 hours. The resulting compound can be purified by washing and recrystallizing the compound from an appropriate solvent.

Examples of the squarium compounds of formula (I) above of this invention include the following compounds.

(1)

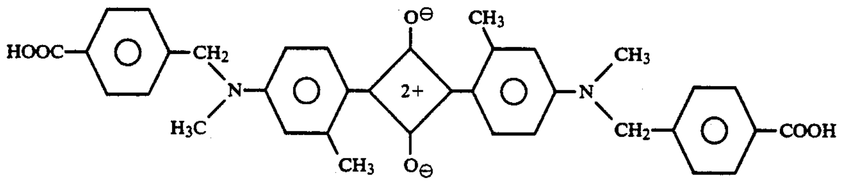

(2)

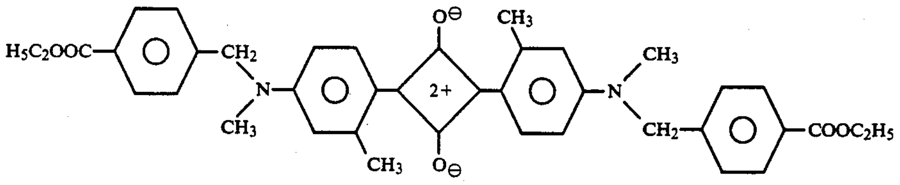

(3)

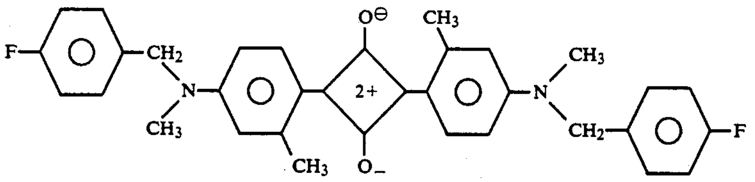

(4)

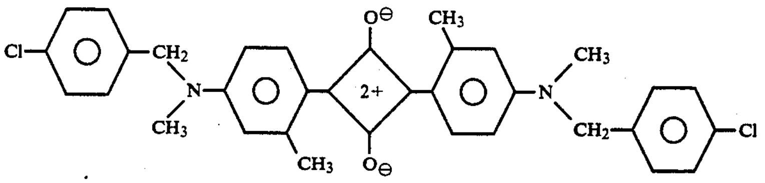

(5)

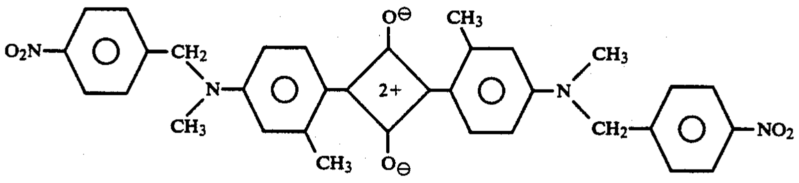

(6)

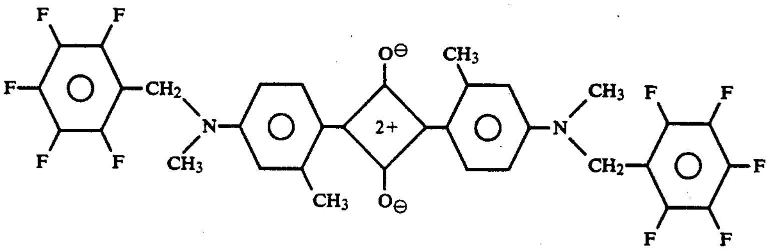

The spectral sensitivity of the squarium compounds of this invention show a flat photosensitivity in the range of from 400 to 850 nm, and the aquarium compounds of this invention have a sufficient photosensitivity in the range from the entire visible ray region to the near infrared ray region.

The squarium compounds of formula (I) can be used in electrophotographic photoreceptors having a multilayer structure. That is, in electrophotographic photoreceptors having a double layer structure consisting of a charge generation layer and a charge transport layer, a combination of the charge generation layer containing a squarium compound of this invention and a known charge transport layer comprising a photoconductive polymer such as a polyvinyldibenzothiaphene, a polyvinylpyrene, a polyvinylanthracene, a polyvinylcarbazole or a layer containing a triarylpyrazoline, a triphenylmethane, an oxadiazole, a tetraphenylbenzidine and a trinitofluorenone, in a binder resin results in the improvement of chargibility of electrophotographic photoreceptors, lowering of residual potential, and further the improvement of mechanical strength.

Figure 1:
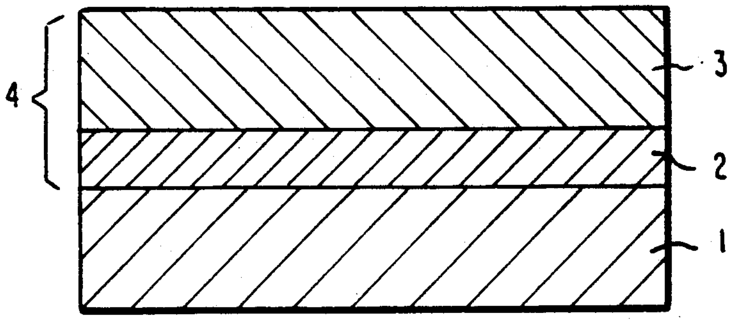
FIGS. 1 and 2 are profile sections of compositions of electrophotographic photoreceptors of this invention.
Figure 2:
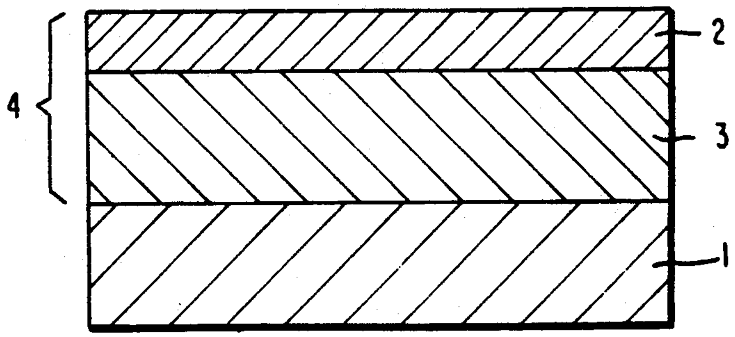

As shown in FIGS. 1 and 2 which explain the construction of electrophotographic photoreceptor of this invention having a double layer structure, a photosensitive layer 4 which is composed of a lamination of charge generation layer 2 containing a squarium compound of this invention and a charge transport layer 3 containing a charge trasport material is provided on an electroconductive support 1. The thickness ratio of the charge generation layer to the charge transport layer is preferably from about ½ to about 1/200. Further, the squarium compound and a charge transport material may be incorporated into one layer to form a single-layered photoreceptor, if desired.

The charge generation layer can consist of a squarium compound alone or a combination of the squarium compound and a binder resin. The ratio of the squarium compound of formula (I) to the binder resin used is from about 10% by weight to about 90% by weight, preferably from about 10% by weight to about 50% by weight.

A solvent coating method and a vacuum evaporation method can be used to prepare the charge generation layer with the squarium compound of this invention without using a binder resin.

The film thickness of charge generation layer is from about 0.1μ to about 3μ, preferably from 0.2μ to 1μ.

For the purpose of its dispersion in a binder, the compound may be ground into fine particles by a known method using any conventional mill, such as an SPX MILL, ball mill or RED DEVIL (trade name). The particle size of the squarium compound is generally not more than 5μ, preferably 0.01 to 3μ, but the particle size is not limited thereto.

The binder used in the charge generation layer may have or may not have photoconductivity. Examples of binders having photoconductivity include photoconductive polymers such as polyvinylcarbazoles, polyvinylcarbazole derivatives, polyvinylnaphthalenes, polyvinylanthracenes, polyvinylpyrene, or other organic matrix materials having a charge transport property.

Moreover, known insulating resins which have no photoconductive property can be used as binders. Examples of such insulating resins include polystyrenes, polyesters, polyvinyltoluenes, polyvinylanisoles, polychlorostyrene, polyvinyl butyrals, polyvinyl acetate, polyvinylbutyl methacrylate, copolystyrene-butadiene, polysulfone, copolystyrenemethyl methacrylate and polycarbonate.

In order to improve mechanical strength of the electrophotographic photoreceptors obtained, a plasticizer can also be used as in the case of ordinary polymeric materials. Examples of plasticizers which can be used include chlorinated paraffin, chlorinated biphenyl, a phosphate plasticizer and a phthalate plasticizer. These plasticizers can be used in an amount of 0 to 10% by weight based on the weight of the binder used without adversely affecting the photosensitivity and electrical properties of the electrophotographic receptors thereby improving the mechanical properties.

The binder having dispersed therein a squarium compound is coated on an electroconductive support. The coating can be performed by a conventional method such as dip method, spray method, bar coater method and applicator method. A good photosensitive layer can be obtained by any of the above methods.

Usable electrically conductive supports include metals (e.g., aluminum, nickel, chromium, iron, stainless, copper, etc.), paper which is rendered electrically conductive, as well as polymeric films and glass plates having an electrically conductive coat of the above metals, Au, Ag, indium oxide, indium tin oxide, etc.

A surface layer such as a protective layer and an insulating layer may further be provided on the light-sensitive layer so as to prevent mechanical damage and chemical change in properties of the light-sensitive layer. The protective layer is a layer having low electric resistance of $10^8$ to $10^{14}$ Ω cm which can be used in the so-called Carlson process, and the insulating layer is an electrically insulating layer which can be used in a process as described in U.S. Pat Nos. 3,041,167 and 3,438,706. Both layers are substantially transparent to light for exposure and the thicknesses of the protective layer and the insulating layer are about 2 to 20μ and about 10 to 40μ, respectively.

In order to prevent injection of electron from an electrically conductive support to the light-sensitive layer, a barrier layer may be formed between the support and the light-sensitive layer. For this purpose, aluminum oxide, nylon and epoxy resins can be used. Such a barrier layer may not be formed when the photoreceptor is used in the process of U.S. Pat. Nos. 3,041,167 and 3,438,706 as described above or when the charge transport layer is formed as a lower layer on the support in the preparation of a double-layered photoreceptor (FIG. 2). An adhesive layer may also be formed between the support and the light-sensitive layer to improve adhesion therebetween.

The electrophotographic photoreceptor of the present invention may be used not only with ordinary copiers but also with laser printers, as well as intelligent copiers since the photoreceptor of the present invention is sensitive to lasers. Laser which can be applied to the photoreceptor of the present invention are preferably semiconductor lasers such as those of Ga-As type semiconductors (e.g., Ga-As, Al-Ga-As, Ga-As-P, etc.).

This invention will now be explained in more detail by the following examples.

EXAMPLE 1

Preparation of Compound (3)

7.92 g of N-(4-fluorobenzyl)-N-methyl-m-toluidine and 2.0 g of squaric acid were heated in a mixture of n-butyl alcohol and toluene with stirring for 5 hours at 100° C. to 120° C. After cooling, greenish crystals precipitated were collected by filtration and then washed with methanol to obtain 0.41 g (4.4% yield) of the desired squarium compound.

Decomposition point: 240° C. to 241° C.

Infrared absorption spectrum (KBr Tablet): γc=o 1630 cm−

Visible absorption spectrum: λ max 647 nm (in dichloromethane solution)

| | Elemental analysis Calc'd (%) | Found (%) |
|---|---|---|
| C | 76.10 | 76.39 |
| H | 5.63 | 5.42 |
| N | 5.22 | 5.01 |

EXAMPLES 2 AND 3

In the same manner as described in Example 1 Compounds (4) and (6) were prepared.

Compound (4)

Decomposition point: 232.5° C. to 233.5° C.

Infrared absorption spectrum (KBr Tablet): γc=o 1590 cm−

Visible absorption spectrum: λ max 647 nm (in dichloromethane solution)

| | Elemental analysis Calc'd (%) | Found (%) |
|---|---|---|
| C | 71.07 | 71.55 |
| H | 5.31 | 5.28 |
| N | 4.29 | 5.08 |

Compound (6)

Decomposition point: 245.0° C. to 245.5° C.

Infrared absorption spectrum (KBr Tablet): γc=o 1590 cm−

Visible absorption spectrum: λ max 639 nm (in dichloromethane solution)

| | Elemental analysis Calc'd (%) | Found (%) |
|---|---|---|
| C | 60.01 | 60.29 |
| H | 3.26 | 3.19 |
| N | 4.12 | 4.03 |

EXAMPLE 4

The squarium compound wherein X is a 4-carboxyl group, n is 1 and R is a hydrogen atom was ground with dichloromethane and steel balls for 12 hours. The ground compound was then added to a polyester resin (Vylon 200, a tradename) in an amount of 30% by weight based on the weight of the polyester resin, followed by mixing, and then the mixture was coated by an applicator on an aluminum plate to prepare a charge generation layer having a thickness of about 0.5 μ (dry basis). A mixture of a polycarbonate resin (Panlite, a tradename) and 1-phenyl-3-[p-diethylaminostyryl]-5-[p-diethylaminophenyl]pyrazoline in an amount of 50% by weight based on the weight of the polycarbonate resin was then coated by an applicator on the charge generation layer to prepare a charge transport layer having a thickness of about 15μ.

The photosensitive surface of this photoreceptor was negatively charged with −6 KV of corona electric discharge for 2 seconds using an electrostatic copy paper test instrument manufactured by Kawaguchi Denki Co., Ltd. After it was allowed to stand for 5 seconds in the dark, its surface potential (Vo) was measured and then a light from a tungsten-halogen lamp of illumination intensity of 10 lux was irradiated to the photosensitizer layer. The time when the value of the surface potential changed to a half the original value was determined to obtain a half value of exposure ($E\frac{1}{2}$). The results obtained were Vo of 655V and E of 6.5 lux·second.

EXAMPLES 5 AND 9

The electrophotographic photoreceptors of these examples were prepared in the same manner as described in Example 4 except that, each of the squarium compounds shown in Table 1 was used, in place of the squarium compound used in Example 4. The electric characteristics of the resulting photoreceptors were determined, and the results obtained are shown in Table 1.

TABLE 1

| Example | Compound No | X | n | R | Vo(V) | $E\frac{1}{2}$ lux·second |
|---|---|---|---|---|---|---|
| Example 5 | 2 | 4-COOC$_2$H$_5$ | 1 | H | 685 | 4.8 |
| Example 6 | 3 | 4-F | 1 | CH$_3$ | 605 | 8.1 |
| Example 7 | 4 | 4-Cl | 1 | CH$_3$ | 715 | 4.7 |
| Example 8 | 5 | 4-NO$_2$ | 1 | CH$_3$ | 670 | 5.6 |
| Example 9 | 6 | F | 1 | CH$_3$ | 730 | 4.4 |

EXAMPLES 10 TO 15

Electrophotographic photoreceptors with inverted order of the charge generation layer and the charge transport layer were prepared in the same manner as those described in Examples 4 to 9 except that the order of the charge generation layer and the transport layer was inverted, and their electric characteristics were measured. The results obtained are shown in Table 2.

TABLE 2

| Example | Compound No | X | n | R | Vo(V) | $E\frac{1}{2}$ lux·second |
|---|---|---|---|---|---|---|
| Example 10 | — | 4-COOH | 1 | H | 620 | 7.1 |
| Example 11 | — | 4-COOC$_2$H$_5$ | 1 | H | 670 | 8.6 |
| Example 12 | 3 | 4-F | 1 | CH$_3$ | 635 | 11.5 |
| Example 13 | 4 | 4-Cl$_2$ | 1 | CH$_3$ | 710 | 8.4 |
| Example 14 | 5 | 4-NO$_2$ | 1 | CH$_3$ | 655 | 10.3 |
| Example 15 | 6 | F | 5 | CH$_3$ | 745 | 7.4 |

While the invention has been described in detail and with reference to specific embodiments thereof, it will be apparent to one skilled in the art that various changes and modifications can be made therein without departing from the spirit and scope thereof.

What is claimed is:

1. A squarium compound represented by formula (I)

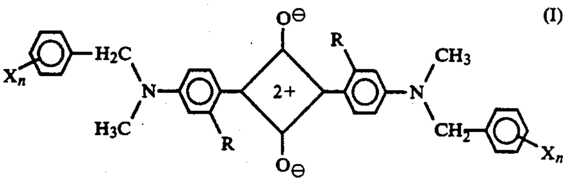

(I)

wherein X represents an electron attractive group, n is 0 or an integer of from 1 to 5 and R represents a methyl group.

* * * * *